US010172698B2

(12) United States Patent
Carton (10) Patent No.: US 10,172,698 B2
(45) Date of Patent: Jan. 8, 2019

(54) METHOD AND SYSTEM FOR MONITORING PREGNANCY TOXAEMIA (71) Applicant: Bernard Carton, Merelbeke (BE)

(72) Inventor: Bernard Carton, Merelbeke (BE)

(*) Notice: Subject to any disclaimer, the term of this patent is extended or adjusted under 35 U.S.C. 154(b) by 0 days.

(21) Appl. No.: 15/241,676

(22) Filed: Aug. 19, 2016

(65) Prior Publication Data

US 2017/0049545 A1 Feb. 23, 2017

(30) Foreign Application Priority Data

Aug. 21, 2015 (GB) .................................. 1514918.0

(51) Int. Cl.
*A61D 17/00* (2006.01)
*A01K 7/02* (2006.01)
(Continued)

(52) U.S. Cl.
CPC ............... *A61D 17/00* (2013.01); *A01K 7/02* (2013.01); *A01K 29/005* (2013.01); *A61B 5/0022* (2013.01); *A61B 5/082* (2013.01); *A61B 5/1128* (2013.01); *A61D 17/006* (2013.01); *G06F 19/00* (2013.01); *G16H 40/67* (2018.01); *A61B 2010/0087* (2013.01); *A61B 2503/40* (2013.01)

(58) Field of Classification Search
CPC .................... A01K 29/005; A01K 7/02; A61B 2010/0087; A61B 2503/40; A61B 5/0022; A61B 5/082; A61B 5/1128; A61D 17/00
USPC .................................................... 340/573.3
See application file for complete search history.

(56) References Cited

U.S. PATENT DOCUMENTS 6,659,039 B1 * 12/2003 Larsen ..................... A01K 5/02
119/51.02
2002/0112668 A1 * 8/2002 van Lenteren ......... A01K 5/015
119/53.5
(Continued)

FOREIGN PATENT DOCUMENTS

CA 2017469 A1 * 1/1991
CN 103759782 A 4/2014
(Continued)

OTHER PUBLICATIONS

Rick J. Rasby, Tory M. Walz, "Water Requirments for Beef Cattle," NebGuide, University of Nebraska Lincoln; Mar. 2011.*
(Continued)

*Primary Examiner* — Nader Bolourchi
(74) *Attorney, Agent, or Firm* — Workman Nydegger (57) ABSTRACT A system for automatically determining pregnancy toxaemia in at least one animal in a group of animals comprises a sensor for obtaining at least one value representative of a liquid or water uptake of the at least one animal, said sensor being adapted to be positioned in the vicinity of a liquid or water supply station or on the at least one animal; and a processing unit configured for comparing the obtained at least one value representative of a liquid or water uptake of the at least one animal to a mean value representative of an average of the at least one value for the group of animals or to a value deduced therefrom; and for generating a signal and/or alert when the obtained at least one value representative of a liquid or water uptake exceeds the mean value or the value deduced therefrom by a pre-determined threshold value.

14 Claims, 4 Drawing Sheets (51) Int. Cl.
*A01K 29/00* (2006.01)
*A61B 5/08* (2006.01)
*A61B 5/00* (2006.01)
*A61B 5/11* (2006.01)
*G06F 19/00* (2018.01)
*G16H 40/67* (2018.01)
*A61B 10/00* (2006.01)

(56) References Cited

U.S. PATENT DOCUMENTS

| | | | |
|---|---|---|---|
| 2004/0154831 A1* | 8/2004 | Seydoux | E21B 7/04 175/24 |
| 2005/0284398 A1 | 12/2005 | Hong | |
| 2006/0052986 A1* | 3/2006 | Rogers | A01K 11/008 702/189 |
| 2006/0201435 A1* | 9/2006 | Arnerup | A01K 7/022 119/71 |
| 2010/0263596 A1 | 10/2010 | Schumann et al. | |
| 2011/0192213 A1 | 8/2011 | Zimmerman et al. | |
| 2012/0299731 A1 | 11/2012 | Triener | |
| 2016/0050888 A1* | 2/2016 | Berckmans | A01K 5/02 119/51.02 |

FOREIGN PATENT DOCUMENTS

| | | | | |
|---|---|---|---|---|
| CZ | 20130956 A3 | 6/2015 | | |
| EP | 0799567 A2 | 10/1997 | | |
| EP | 1234497 A2 | 8/2002 | | |
| EP | 1543721 A1 | 6/2005 | | |
| GB | 2541459 A | * 2/2017 | | G01N 37/00 |
| KR | 20130089754 A | 8/2013 | | |
| NL | 1008840 C2 | 10/1998 | | |
| WO | 2004095916 A1 | 11/2004 | | |
| WO | 2006023878 A1 | 3/2006 | | |
| WO | 2010091686 A1 | 8/2010 | | |
| WO | 2014153626 A2 | 10/2014 | | |

OTHER PUBLICATIONS

Great Britain Search Report from GB Application No. GB1514918.0, dated Jun. 6, 2016.
Sargison, "Pregnancy Toxaemia", Diseases of Sheep, Chapter 52, 2007, Blackwell Publishing Ltd, pp. 359-363.
Schoenian, "Pregnancy Toxemia in Ewes and Does", Maryland Small Ruminant Page, www.sheepandgoat.com, 2002, 2 pages.
Great Britain Search Report from GB Application No. GB1514918.0, dated Feb. 25, 2017.
Great Britain Search Report from GB Application No. GB1514918.0, dated Feb. 26, 2017.

* cited by examiner

METHOD AND SYSTEM FOR MONITORING PREGNANCY TOXAEMIA

FIELD OF THE INVENTION

The present invention relates to a method and system for monitoring pregnancy toxaemia, preferably in ewes and/or does. More specifically it relates to an automated pregnancy toxaemia (ketosis) monitoring method and system.

BACKGROUND OF THE INVENTION

Pregnancy toxaemia in sheep and goats has also been called ketosis, lambing/kidding sickness, pregnancy disease and twin-lamb/kid disease. It occurs in all parts of the world and is an often fatal disease occurring during the last months of pregnancy. Death occurs in two to 10 days in about 80 percent of the cases. Pregnancy toxaemia is characterized as a metabolic disorder caused by low glucose concentrations in the blood and excessive breakdown of body fat to compensate, whereby "ketones" are the toxic by-product produced during this rapid breakdown of fat. Economic losses because of the disease have been considerable, and it is the most commonly occurring metabolic disease of sheep and goats.

Inadequate nutrition during the last one-third of pregnancy is the primary cause of low blood sugar/pregnancy toxaemia, as ewes and does cannot consume enough energy to meet the demands of their growing foetus(es). This is because approximately 70 percent of foetal growth occurs during the last 4 to 6 weeks of pregnancy. Over-conditioned ewes and does are susceptible to pregnancy toxaemia because of malfunctioning of the liver. Under-conditioned ewes are also susceptible as they cannot eat enough to meet their own nutritional needs, let alone the added burden of developing foetuses. Ewes and does carrying multiple births are also at high risk for pregnancy toxaemia. Ewes with triplet foetuses require 230% more energy than ewes with single foetuses. Actually, anything that affects the ewe's or does' ability to eat enough during late gestation can result in pregnancy toxaemia: multiple foetuses, fat ewes/does, thin ewes/does, small ewes/does, timid ewes/does, granny ewes/does, dental disease, parasitism, and/or lack of exercise as described by Susan Schoenian in "*Pregnancy toxaemia in ewes and does*" (2002 online article).

In order to prevent pregnancy toxaemia, nutrition management of the animals is beneficial, whereby the ewes/does are provided adequate energy in their ration during the last 4 to 6 weeks of gestation. The latter is accomplished for instance by grouping the ewes/does in function of the amount of foetus(es) and providing adapted nutrition with the addition of concentrates if needed. In order to group the ewes/does in an appropriate nutrition group an ultrasound scan may be performed between days 35 and 55 of gestation. However, after the grouping a miscarriage might occur (possible as a result of the scan) or the scan might have provided incorrect information (i.e. counting the same foetus twice or counting two different foetuses as one), therefor still resulting in mal-nutrition of the ewe/does and the presence of pregnancy toxaemia.

Treatment of pregnancy toxaemia may comprise a cesarean section or induced abortion to remove the nutritional drain on the mother or by providing energy in the form of glucose or glucose precursors up to kidding of the ewe or doe, as by, for example, intravenous glucose or dextrose injections, oral administration of propionate, glycerol, propylene glycol, molasses, etc.

Therefor there is a need for novel methods and systems for monitoring and/or preventing pregnancy toxaemia.

SUMMARY OF THE INVENTION

It is an object of embodiments of the present invention to provide methods and systems for monitoring sheep and/or goats for pregnancy toxaemia. The above objective is accomplished by a method and device according to embodiments of the present invention.

Embodiments of the present invention provide systems and methods for monitoring pregnancy toxaemia, using at least one value representative of a liquid or water uptake of at least one animal. In preferred embodiments the at least one value is a drinking frequency of the animal, for example the amount of times the animal consumes or drinks liquid or water. This drinking frequency can be monitored per day or per other suitable timeframe. In other particular embodiments the at least one value is a drinking amount, e.g. the amount of water an animal has consumed in a timeframe or period, like for example the amount of water consumed per day. In other embodiments, the at least one value representative of a liquid or water uptake, can be a combination of the drinking frequency and drinking amount.

In a first aspect, the present invention provides a system for automatically determining pregnancy toxaemia in at least one animal in a group of animals, the system comprising:

a sensor for obtaining at least one value representative of a liquid or water uptake of the at least one animal, said sensor being adapted to be positioned in the vicinity of a liquid or water supply station or on the at least one animal; and a processing unit configured for comparing the obtained at least one value representative of a liquid or water uptake of the at least one animal to a mean value representative of an average of the at least one value for the group of animals or to a value deduced therefrom; and generating a signal and/or alert when the obtained at least one value representative of a liquid or water uptake exceeds the mean value or the value deduced therefrom by a pre-determined threshold value.

Scientific literature teaches that for instance sheep or goats have a daily water uptake of about 0.5 to 1.5 liter, depending on the type of basic nutrition and the environment. Such water uptake can take place once a day, or can be spread over a plurality of moments. Hence in the context of the present invention, the at least one value representative of a liquid or water uptake could either be the drinking frequency, e.g. once a day, or a drinking amount, e.g. between 0.5 and 1.5 liter per day.

At the end of the pregnancy, the need for more water rises in function of the number of lambs being carried, up to 1 to 2 liter per day, according to literature. Again, in the context of the present invention, the at least one value representative of a liquid or water uptake could either be the drinking frequency, e.g. once a day, or a drinking amount, e.g. between 1 and 2 liters per day.

Embodiments of the present invention are based on the insight that animals, like e.g. sheep and/or goats, having pregnancy toxaemia show a change in liquid or water uptake, more specifically for instance a change in the frequency of drinking. Depending on the basic nutrition, a change in drinking frequency of at least 20%, for instance more than 30%, such as between 30% and 75%, or between 30% and 50%, can be observed in animals suffering from pregnancy toxaemia. This symptom has not been identified in any prior art.

In accordance with embodiments of the present invention, the at least one value representative of a liquid or water uptake of a particular animal, is compared to a mean value representative of an average of the values representative of a liquid or water uptake of the animals in the group of animals, or to a value deduced from this mean value, for instance a value equal to the mean value increased by a threshold value, for instance a 30% increase of the mean value. In the first case, i.e. when the value representative of liquid or water uptake of a particular animal in the group is compared to a mean value for this liquid or water uptake for the group of animals, a signal and/or alert may be generated if this mean value is exceeded by a pre-determined threshold value, for instance by at least 20%, at least 25%, at least 30%. In the second case, i.e. when the value representative of liquid or water uptake of a particular animal in the group is compared to a value deduced from the mean value for this liquid or water uptake for the group of animals, for instance it is compared to the mean value increased by a threshold value of at least 20%, a signal and/or alert may be generated if this value deduced from the mean value reached or is exceeded by any value.

In embodiments of the present invention, the threshold value will have to be selected depending on the animal population, their location, and their basic nutrition, but can for instance be at least a 20% increase, for instance at least a 25% increase, or at least a 30% increase, such as between 30% and 50% increase on the mean value representative of an average for the group of animals of the at least one value representative for water uptake. It is an advantage of a system according to embodiments of the present invention that pre-clinical pregnancy toxaemia of an animal, such as an ewe of doe, can be detected in a non-contact, non-invasive way (no blood or urine samples are to be taken), by simply monitoring the drinking pattern or behavior of a doe or ewe.

It is an advantage of a system according to embodiments of the present invention that the presence of pregnancy toxaemia, and more specifically ketoacidosis, can be traced in real time and can proactively provide information of the health of an animal or group of animals, even when not present or from a distance.

It is an advantage of the system that large flocks of sheep/goats (i.e. in the tens, hundreds, even thousands) can be monitored automatically for pregnancy toxaemia, and pregnancy toxaemia can be prevented pro-actively. Embodiments of the present invention advantageously provide additional inspection means for the shepherd and additional ease of mind. During lambing, a shepherd is responsible for 250 to 300 ewes. Controlling and monitoring these ewes day and night is very stressful, definitely when taking the lambing into account which can be between 4 to 6 weeks. An alert shepherd can recognize ewes having pregnancy toxaemia symptoms; however, the presence of recognizable symptoms is an indication that the toxaemia is in an advanced state. The present invention provides methods and devices for enabling pre-clinical determination of pregnancy toxaemia.

A system according to embodiments of the present invention may further comprise an identification unit for identifying the at least one animal, the identification unit being adapted to be positioned in the vicinity of a liquid or water supply station or on the at least one animal. The processing unit may be configured for determining the at least one animal for which the signal and/or alert is generated.

A system according to embodiments of the present invention may further comprise a breath analyzer for analyzing the breath of the at least one animal.

In a system according to embodiments of the present invention, the sensor may be provided in a compact cylindrical valve device that is adapted to be removably attached to a water supply line and delivers water, on demand, into the animal's mouth through a hollow control device and is adapted to obtain the at least one value representative of a liquid or water uptake.

In a system according to embodiments of the present invention, the sensor may be coupled or removably connected between a compact cylindrical valve device and a water supply line.

In a system according to embodiments of the present invention, the sensor may be provided at a water supply site, for example a water supply line or hose which supplies water, which is connected, for example through the sensor, with a water supply station. In preferred embodiments the sensor is adapted to couple, preferably removably, a water supply line, for example a water hose, and a water supply station.

In a second aspect, the present invention provides a water supply station for at least one animal, said water supply station comprising:
an identification unit for identifying the at least one animal approaching or standing at the water supply station;
a sensor for obtaining at least one value representative of a liquid or water uptake of the at least one animal; and
a processing unit configured for
comparing the obtained at least one value representative of a liquid or water uptake of the at least one animal to a mean value representative of an average of the at least one value for the group of animals or to a value deduced therefrom; and
generating a signal and/or alert when the obtained at least one value representative of a liquid or water uptake exceeds the mean value or the value deduced therefrom by a pre-determined threshold value, and therefore determining that a problem occurs with the at least one animal, more particularly that that the at least one animal suffers from pregnancy toxaemia.

In this aspect, the meaning of "a value representative of a liquid or water uptake", "a mean value representative of a liquid or water uptake", "a value deduced from such mean value", and the "threshold value" is as explained with reference to the first aspect, and is not repeated here for sake of brevity.

A water supply station according to embodiments of the present invention may further comprise a breath analyzer for analyzing a breath sample of the at least one animal.

In a water supply station according to embodiments of the present invention, the sensor may be provided in a compact cylindrical valve device that is adapted to be removably attached to a water supply line and delivers water, on demand, into the animal's mouth through a hollow control device and is adapted to obtain at least one value representative of a liquid or water uptake.

In a water supply station according to embodiments of the present invention, the sensor may be coupled or removably connected between a compact cylindrical valve device and a water supply line of the water supply station.

In a water supply station according to embodiments of the present invention, the sensor may be provided at a water supply site, like for example a water supply line, of the water supply station of the water supply station.

In a third aspect, the present invention provides a water dispenser, also known as a nipple, comprising a sensor. The water dispenser comprises a compact cylindrical valve device that is adapted to be removably attached to a water supply line and delivers water, on demand, into an animal's mouth through a hollow control device. The sensor may then be provided so as to obtain at least one value representative of a liquid or water uptake.

A water dispenser in accordance with embodiments of the present invention may be adapted to communicate with, or may comprise, a processing unit configured for comparing the obtained at least one value representative of a liquid or water uptake of the at least one animal to a mean value representative of an average of the at least one value for the group of animals, or to a value deduced therefrom; and generating a signal and/or alert when the obtained at least one value representative of a liquid or water uptake exceeds the mean value or the value deduced therefrom by a pre-determined threshold value, and therefore determining that a problem occurs with the at least one animal, more particularly that the at least one animal suffers from pregnancy toxaemia.

In this aspect, the meaning of "a value representative of a liquid or water uptake", "a mean value representative of a liquid or water uptake", "a value deduced from such mean value", and the "threshold value" is as explained with reference to the first aspect, and is not repeated here for sake of brevity.

In a fourth aspect, the present invention provides a water supply line, like for example a water hose, comprising a sensor. The sensor is coupled and/or removably attached with the water supply line and is adapted to obtain at least one value representative of a liquid or water uptake. Advantageously, such a water supply line comprising a sensor can be removably attached or coupled to water supply stations known in the art, such that one is enabled to obtain at least one value representative of a liquid or water uptake.

In a fifth aspect, the present invention provides the use of a value representative for liquid or water uptake of an animal as an indication of the presence of pregnancy toxaemia of said animal, for instance a pregnant ewe or doe. The value representative for liquid or water uptake is liquid or water uptake frequency.

In a sixth aspect, the present invention provides a method for automatically monitoring pregnancy toxaemia in at least one animal, for instance pregnant ewe or doe, in a group of animals. The method comprises:

obtaining at least one value representative of a liquid or water uptake of the at least one animal;

comparing the obtained at least one value to a mean value representative of an average of the at least one value for the group of animals or to a value deduced therefrom; generating a signal and/or alert when the at least one value representative of a liquid or water uptake exceeds the mean value or the value deduced therefrom by a pre-determined threshold value.

A method according to embodiments of the present invention may further comprise identifying the at least one animal with pregnancy toxaemia.

It is an advantage of a method according to embodiments of the present invention that the presence of ketoacidosis can be detected in a non-invasive way by monitoring a drinking pattern or behaviour of an animal such as a doe or ewe. As pre-clinical pregnancy toxaemia is traced or determined or in other words when the presence of ketoacidosis is confirmed as result of a changed drinking pattern (e.g. a more frequent water uptake or a greater volume of water uptake), one has more time to improve the situation of the ewe or doe than would be case when known early clinical symptoms, such as grinding of the teeth, would occur. It is an advantage that pregnancy toxaemia can be determined non-invasively and thereby confirming the presence of acidosis with minimal ketones. It is an advantage of the method according to embodiments of the present invention that possible interpretation errors made during an ultrasound scan, like diagnosing twin pregnancy while in fact there is a triple pregnancy, can be traced.

It is an advantage of embodiments of the present invention that an automated method is provided which is automatic, resulting in less working hours, stress and costs when managing the animals.

In a method for automatically monitoring pregnancy toxaemia according to embodiments of the present invention, the at least one value is a drinking frequency, drinking time, drinking volume or a combination thereof.

A method for automatically monitoring pregnancy toxaemia according to embodiments of the present invention may further comprise analyzing a breath sample of the at least one animal and generating a signal and/or alert when acetone particles are found in the breath sample indicating pregnancy toxaemia.

A method for automatically monitoring pregnancy toxaemia according to embodiments of the present invention may further comprise adapting a feed supply of the at least one animal when pregnancy toxaemia is determined. This way, accurate nutrition supply per animal can be obtained and altered if needed, in a most optimal way.

In particular embodiments of the present invention, the average of the at least one value representative of a liquid or water uptake for the group of animals may be obtained at least 6 weeks before kidding of the at least one ewe or doe. This may provide more reliable results.

In a method for automatically monitoring pregnancy toxaemia according to embodiments of the present invention, the average of the at least one value representative of a liquid or water uptake for the group of animals may also be obtained by using the same system as used for performing the method of embodiments of the present invention, for the group of animals.

In a further aspect, the present invention provides a computer program product that, if implemented on a control or processing unit of a system according to embodiments of the first aspect of the present invention, enables performing a method according to embodiments of the fifth aspect of the present invention.

The present invention furthermore provides a data carrier storing a computer program product according to embodiments of the present invention.

The present invention also provides transmission of such computer program product according to embodiments of the present invention over a network.

It is an advantage of embodiments of the present invention that pregnancy toxaemia can be detected in a pre-clinical stage, by simply counting water or liquid drinking frequency of an animal, preferably an ewe or doe, to calculate a water drinking amount, which can easily be determined. No actions need to be taken which could scare the animal.

It is an advantage of embodiments of the present invention that normal birth weights are obtained and less complications at kidding.

It is an advantage of embodiments of the present invention that feeding of animals can be precisely controlled and fine-tuned. As a result, a tailored feeding scheme can be set up.

It is an advantage of embodiments of the present invention that very early detection of acidosis is possible, more specifically before actual symptoms occur (cf. pre-clinical state).

It is an advantage of embodiments of the present invention that the presence of pregnancy toxaemia and more specifically ketoacidosis can be traced in real time and can proactively provide information of the health status of the animal.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "pregnancy toxaemia", reference is made to the description for example provided by N. D. Sargison in p. 359 of "*Diseases of Sheep*" (Blackwell publishing 2007 edited by Ian Aitken), which describes a process comprising mobilization of lipids and production of free fatty acids which are taken to the liver and oxidized with the tri-carboxylic acid cycle to provide energy as acetyl co-enzyme A (acetyl CoA). This biochemical pathway is dependent on a constant supply of oxaloacetate from propionate and production of aceto-acetyl CoA. Hydrogenation of aceto-acetyl CoA results in the formation of BOHB and acetoacetate, with acetone formed by decarboxylation. While these ketones can be metabolized, their excessive production, combined with liver insufficiency die to the accumulation of triglycerides that accompanies lipolysis, leads to their accumulation proportional to the dietary carbohydrate deficit. During the final 6 weeks of pregnancy plasma concentration of BOHB less than 0.8, 0.8-1.6 and greater than 1.6 mmol/1 represent respectively adequately nourished, moderately undernourished and severely undernourished ewes. BOHB and acetoacetate are strong acids. Furthermore, prolonged urinary excretion of ketone bodies results in the loss of sodium and potassium ions, lowering the plasma alkali reserve. The resulting ketoacidosis causes dyspnea and exacerbates the hypoglycaemic central nervous system depression, progressing to an irreversible stage, where there is dehydration and uraemia, often compounded by fetal death and autolysis in utero, toxaemia and metritis. Accordingly, embodiments of the present invention can also be used by a skilled person to obtain an indication of BOHB values or the BOHB values can be used a point of reference when comparing obtained results using systems and methods of the present invention.

Where in embodiments of the present invention reference is made to "average", reference is made to a measure of central tendency. The term average may refer to a median, mode, or another central or typical value. In statics the median, the mode, and the mid-range can be used in addition to the mean as estimates of central tendency in descriptive statistics.

Embodiments of the present invention provide methods and systems to prevent and/or monitor pregnancy toxaemia in livestock, more preferably in sheep or goat flocks and specifically pregnant ewes or does. The latter is enabled by monitoring the water or fluid uptake behaviour of a pregnant ewe or doe and comparing said value to the average water or fluid uptake of a group or flock of pregnant ewes or does preferably 5 to 6 weeks before kidding. Embodiments of the present invention are particularly advantageous for sheep or goat breeders, whereby the sheep or goat breed is susceptible for pregnancies resulting in multiple births (i.e. a plurality of foetuses). Embodiments of the present invention are particularly advantageous for sheep or goat breeders who put their pregnant ewes and does inside the stable at the end of the gestation period (i.e. 5 to 6 weeks before kidding), for instance from end of December to end of March. This trend of putting pregnant ewes and does inside a stable is gaining in popularity among breeders as it enables an environment of controlled nutrition intake of the animals (i.e. in function of the amount of foetuses to be kid) and as a direct result also does not interfere with the grass-production of the new season.

Obtaining a value representative of a water or liquid uptake or a value representative of the drinking behaviour of at least one animal or group of animals can be accomplished by for instance implementing sound or vibration detection and recognition techniques to measure and identify water or liquid uptake signals, such as sounds or vibrations, preferably resulting from a water or liquid uptake action of at least one animal drinking from a drinking supply station as described in WO 2014/153626. Optionally, information on the presence, position and movements of animals within the vicinity of the water or liquid supply station can be combined with the analysis of said sound or vibration data to further improve the estimation of the water or liquid intake by monitoring how many animals are located at the nutriment, and preferably water, supply station and whether the animals are in an eating or drinking location and/or position.

A sound, such as an impact sound, or another acoustic signal, is emitted as a result of the animal taking up water or liquid from a supply station, such as when drinking. Such a water or liquid uptake associated sound, may be captured using a suitable sensor, for instance a microphone, located in the proximity of the supply station, preferably integrated in or attached to the supply station. In other embodiments, the sensor, e.g. microphone, may also be positioned on the animal of which the drinking behaviour is to be studied.

Optionally, the method of the present invention further may provide in other embodiments the use of a system for detecting the presence and position of an animal at the water or liquid supply system, preferably at the moment said water or liquid uptake signal is detected. More particularly the method of the present invention may involve the use of an automated image monitoring system comprising at least one still or video camera, which in conjunction with a computing means allows detecting the presence and position of an animal at a water or liquid supply system. Preferably, said camera is pointed at the supply station, preferably arranged in such a way as to provide a top-view image of the nutriment, and more preferably water, supply system and the nearby animal or animals. Advantageously, in this way, information is provided about the presence and position of animals near the supply station, including but not limited to the number of animals at the supply station and the duration and frequency of the water or liquid uptake. Preferably, the presence and position of an animal or group of animals at the water supply system, such as the closeness of the at least one animal to the water or liquid supply system and the direction from which it/they approach, may be monitored using image analysis. Said image analysis typically comprises the steps of subtraction of the background and determination of threshold size of objects to distinguish the animals (so that only animals are detected). By applying a segmentation algorithm, animals are separated in the captured image and the duration of the animal staying and drinking at the water supply system can be calculated. Preferably, the analysis of the image data is combined with the analysis of said vibration and/or impact sound data in order to improve the accuracy of the nutriment, and more preferably water, uptake estimation. For instance, it may improve the accuracy when a detected water or liquid uptake signal is ignored in case the analysis of the image data indicates that no animals are present at the nutriment, and more preferably water, supply station. Preferably, the detection and analysis of said water or liquid uptake signal, the combination thereof with the image analysis data and the extrapolation of the water intake is performed in real-time or semi-real time, wherein fragments of data are recorded and processed in segments.

In yet further embodiments the water or liquid intake of at least one animal can be obtained by weighing the water or liquid container before and after a drinking session and obtaining the volume of water consumed and thus a value representative of a liquid or water intake. In alternative embodiments a platform whereon the at least one animal is positioned can be weighed before after and after a drinking session so as to obtain a water or liquid uptake value. In other embodiments an electric drinkometer may be used to obtain a value representative of the drinking behaviour of the at least one animal. Preferably such a drinkometer or oral metering device is provided permitting electrical isolation of the animal from the recording system. In preferred embodiments a fluid dispensing system for livestock may be provided that yields reliable and accurate measures of fluid consumption. Fluid may be taken by licking or by sucking, whereby the fluid dispensing system can be attached to a standard drinkometer sensing circuit. Such a fluid dispenser advantageously permits accurate measurement of the total volume of fluid consumed over a specified period of time. In addition to measuring the total volume of fluid consumed at a specific frequency and duration, a drinking pattern may also be provided.

In further embodiments, a sensing device 50 for obtaining a value representative of the drinking behaviour of at least one animal, e.g. of the liquid or water uptake, may be provided or positioned in a fluid dispenser 70, like for example, but not limited thereto, a compact cylindrical valve device 80 that is adapted to be removably attached directly to a water supply line. The cylindrical valve is preferably adapted to deliver fluid such as water, for example on demand, directly into the animal's mouth through a hollow control device 90. As a result, it is possible to obtain at least one value representative of a liquid or water uptake. Such a compact cylindrical valve may be in the form of a flexible nipple.

A sensing device used in such a fluid dispenser may for example be a fluid sensor or an oral fluid metering device. Such a sensing device may operate by means of pressure sensing, where a change in pressure may represent a drinking activity.

In embodiments of the present invention each time an animal drinks water, for example by using a water dispenser, the sensing device is operative to obtain a water uptake frequency and/or a water uptake amount, whereby the frequency is obtained by counting the number of times per day the animal drinks water. Identifying an animal can be performed when the animal is drinking or has finished drinking, such that any deviating drinking behaviour can be linked to an identified animal.

In embodiments of the present invention the drinking behaviour of the at least one animal may be monitored by use of imaging means and/or sound sensors; however said imaging means may also be used to identify said animal, for instance by taking an image of a tag comprising an identification number in the ear or around the neck of the animal taking up water and processing said image and obtaining therefrom an identifier, e.g. an identification number, and comparing the latter with a database comprising identifiers and corresponding animals.

In other embodiments the at least one animal may be wearing identification means in the form of radio-frequency identification (RFID) transponders or tags whereby the system of the present invention provides a RFID reader such to identify such animal. Such RFID transponders or tags help manage, identify and safeguard livestock. Preferably glass tag RFID are used, more specifically low frequency transponders effective for bolus use, as well as high performance tags for subcutaneous placement, or livestock ear tag placement for sheep and goats. Embeddable transponders can also be used which can be housed in ear tags for custom form factors using various materials to create specialized low frequency tags. Glass tag units used in embodiments of the present invention may be enclosed in biocompatible glass, making them harmless to animals. The skilled person can also develop a custom tag solution to fit application requirements for chip type, dimensions, programming and materials.

When the at least one value representing a water or liquid uptake of the at least one animal is obtained, the at least one value is compared to a mean value or a value deduced therefrom. The mean value provides an average of the obtained at least one value, representative of the behaviour of the group of animals for said at least one value of which the animal is a member. This average can be measured by using the methods and systems of the present invention applied to a group of animals comprising a plurality of members, for instance at least 10 members, at least 50 members, at least 100 members; or by using a look-up table providing an expected average value for the at least one value representing the water or liquid uptake. The expected average value can be provided at design time. Large animal breeding farms provide their own average values, based on the type of nutrition fed to the animals. This expected average value can thus be provided experimentally, preferably in real-time, or can be a value provided in literature or a saved value for other comparable groups of animals. As the drinking behaviour of at least one animal is strongly dependent on the feed of the at least one animal, obtaining a value representative of the drinking behaviour of the at least one animal or group of animals (e.g. average) is preferably done when a feeding plan of said animal or group of animals is altered or set for the first time. In embodiments of the present invention said value representative of the drinking behaviour, e.g. the average value, can be obtained more than once in time, providing the dependency of the drinking behaviour of a group of animals in time during gestation. A value deduced from the mean value may for instance be the mean value increased by a pre-determined threshold value. This way, the value deduced from the mean value be a value representative of a pregnancy toxaemia threshold.

When the at least one value representing a water or liquid uptake is, for instance, a drinking frequency and a drinking period, the obtained values of at least one animal are provided as well as the average value of both parameters for the group of animals, of which the at last one animal is a member. Thereafter, a comparison of both values, e.g. drinking behaviour of the at least one animal as compared to the general or average drinking behaviour of the group of the animals, or as compared to values deduced thereof, is provided. When the measured values of the at least one animal exceed said average by a pre-determined threshold, within acceptable error margins, the presence of pregnancy toxaemia or ketosis is indicated. Then, in accordance with embodiments of the present invention, a signal and/or alert is automatically generated so as to indicate that a dangerous ketosis limit has been reached. In particular embodiments an alert signal is generated and transmitted to a mobile device, like for instance via an app on the mobile device such as a cell phone or a tablet, so as to provide an indication of deviating drinking behaviour of a particular animal. In further preferred embodiments an alert, e.g. an auditory alert of a visual alert, e.g. also via the app, is generated when presence of acetone is determined.

When the mean value or the value deduced therefrom is exceeded by a pre-determined threshold value in embodiments of the present invention, a visual device like a lamp may be activated, causing a visual alert signal to be producer, or an audio device like a buzzer, a hooter or a horn may be operated, causing an audible alert signal to be produced, or both. Both of the devices may be called a warning device. Either the audible alert signal or the visual alert signal or the combination of the audible alert signal and the visual alert signal may be called an alert signal.

The herder of the flock or the livestock may respond to the audible alert signal and/or the visual alert signal by providing glucose to the identified animal which has reached a dangerous limit of ketosis and/or by changing its nutrition scheme.

Alternatively, rather than activating visual or audio devices, a device or system according to embodiments of the present invention may be adapted to transmit the results of the comparison, or a warning signal triggered therefrom, either via cable or wirelessly, via Bluetooth or any other suitable means, to an electronic device, for instance a portable device such as a smartphone, a tablet, a laptop, or to another processing device, or to the cloud within seconds. The portable device may be carried by the herder of the flock or the livestock, or the transferred information may be easily accessible by him.

In yet further embodiments, the present invention may further comprise analyzing a breath sample of the at least one animal for the presence of acetone particles indicative of ketosis, as when an animal is in ketosis its breath may smell of acetone (acidosis). This is due to the breakdown of acetoacetic acid into acetone and carbon dioxide which is exhaled through the lungs. In embodiments of the invention, a breath analyzing sensor like for instance a gas sensor may be used which is adapted to trace acetone particles. In preferred embodiments chemo-resistive gas sensors made of nanostructured metal-oxide semiconductors may be used. In alternative embodiments a device can be used, powered for instance by batteries, comprising a pressure sensor to detect when an animal breathes into it, and at least one type of semiconductor-based gas sensors that is capable of detecting acetone concentrations. Depending on the sensors used, a specific minimal concentration of acetone is preferably present so as to enable a measurement. In a specific example of a sensor for detecting acetone a minimal concentration of 0.2 to 50 parts-per-million of acetone are preferred to detect acetone presence. After detecting the exhaled breath, the device may provide an alert signal and/or transmit the results when acetone presence is detected, either via cable or wirelessly via Bluetooth or any other suitable way, to an electronic device, for instance a portable device such as a smartphone, or to another processing device, or to the cloud, within seconds.

Figure 1:
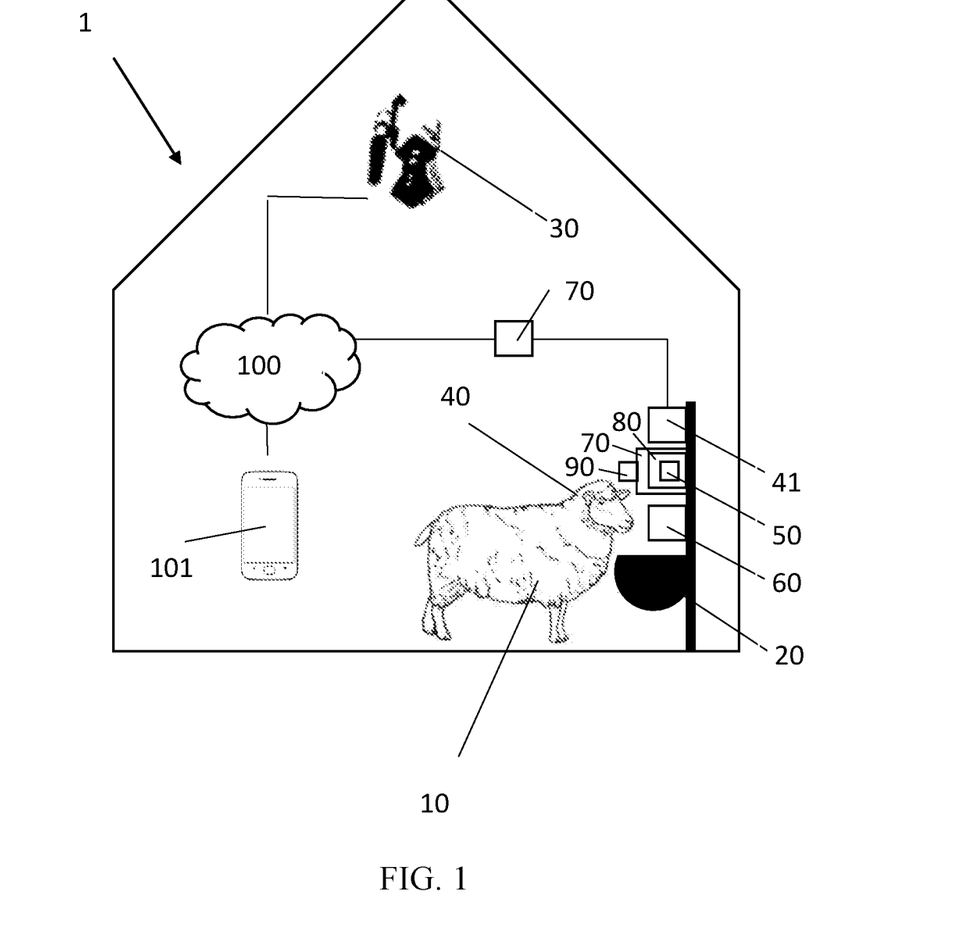
FIG. 1 schematically illustrates a stable comprising a system, more specifically a water or liquid supply station, according to embodiments of the present invention.

FIG. 1 schematically illustrates a system according to embodiments of the invention, used in a stable 1 for monitoring at least one pregnant ewe 10 in a flock of ewes, whereby the flock of ewes is a flock of ewes which are categorized in function of the amount of foetuses they carry. The group of animals, as referred to in this text, preferably is a group of pregnant ewes or does, the group of ewes or does comprising the same amount of foetuses, which are for instance determined by an ultrasound. In a specific embodiment, the drinking behaviour of at least one ewe 10 in the group of ewes is monitored at the water or liquid supply station 20. The water supply station 20 may comprise a sensor 50, for instance a microphone or a liquid sensor, or an electronic drinkometer, for monitoring the drinking behaviour of the at least one pregnant ewe. When particular types of sensors 50, for instance a microphone, are used for measuring a value of a liquid or water uptake, the latter may also be positioned on the ewe (not shown) instead of in the vicinity of the water supply station. The drinking behaviour of the animals may further be monitored using a camera 30, as illustrated in FIG. 1. Said camera 30 may also be used to identify the ewe 10 taking up water or liquids. Moreover, said camera 30 may also be used to monitor any abnormal behaviour of the ewe indicative of pregnancy toxaemia.

In embodiments of the present invention, the system comprises an identification unit 41 for identifying an animal approaching or present at the water or liquid supply station 20. In preferred embodiments, the ewe 10 may carry an identification tag 40, e.g. an RFID identification tag, for instance in its ear, and the system according to embodiments of the present invention comprises a reader 41 for reading the identification tag 40.

Figure 3:
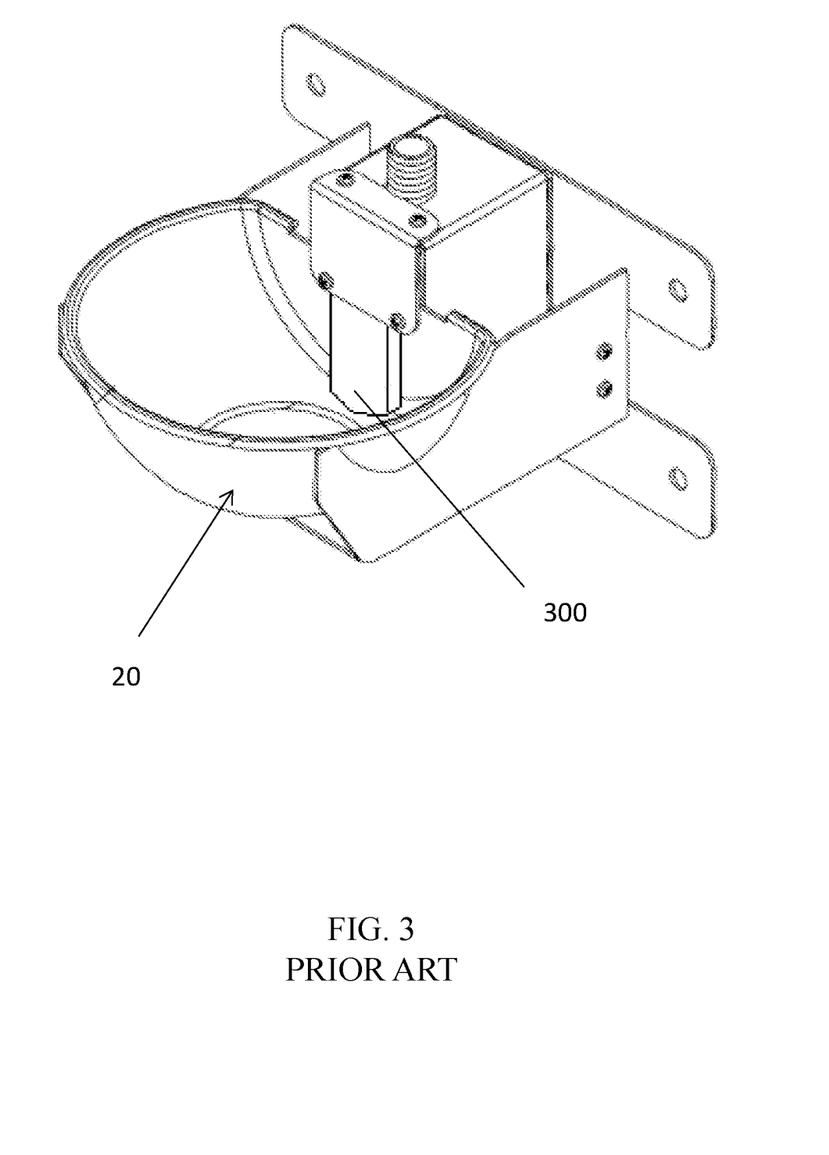
FIG. 3 illustrates a water or liquid supply station known in the art, which may be used in embodiments of the present invention.

The water supply station 20 may further comprise a gas sensor 60 for measuring acetone traces in the ewes' breath, indicative of pregnancy toxaemia or ketosis. Preferably all used devices 30, 40-41, 50, 60 are wireless and provide output values, which may be saved and categorized in a cloud 100, which can be accessed via a computing device 101, for instance a portable device, such as a smartphone, via an app. FIG. 3 shows an example of a water supply station 20 known in the art, which uses a nipple system 300 to dispense water and which comprises a water bowl. Such systems may optionally comprise a container under each water dispenser to collect water wastage (not shown). According to some embodiments of the invention a sensing device (not visible in FIG. 3) is preferably provided in the nipple system 300 so as to enable determination of a water uptake parameter of the animal, like for instance duration of water uptake and/or frequency of water uptake and/or amount of water uptake. In alternative embodiments of the invention a sensing device (not visible in FIG. 3) is preferably provided at a water supply site of a water supply station 20.

Figure 4:
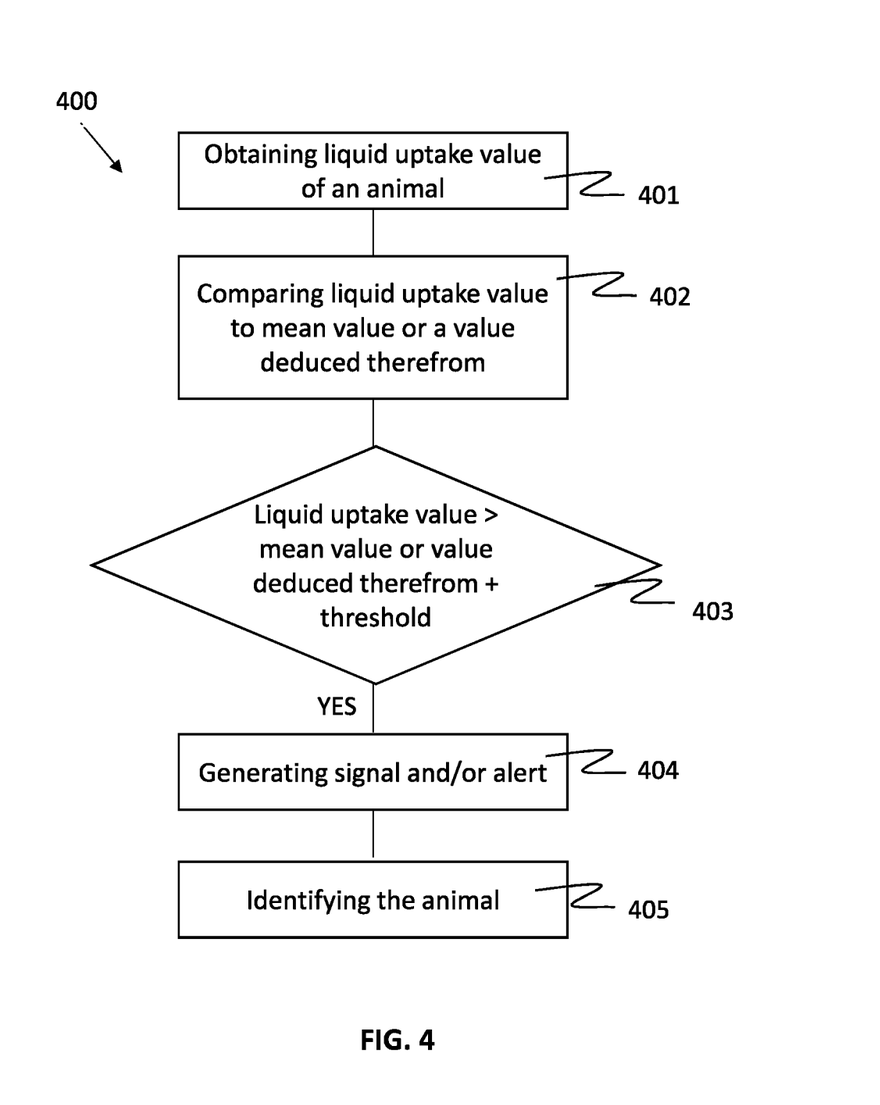
FIG. 4 is a schematic overview of a process flow according to methods of the present invention.

A general overview of a process flow 400 of methods according to embodiments of the present invention is given in FIG. 4. In a first step 401 a water or liquid uptake value is obtained, like for example a frequency of water uptake by a particular animal over time. In a second step 402, the value representative of a water uptake is then compared to a reference value which is representative for a group of animals without pregnancy toxaemia, for instance a mean value representative of an average of the liquid uptake value for the group of animals, or a value deduced from this average value. In a third step 403 a decision is taken about whether the liquid uptake value is larger than the reference value, and exceeds this reference value by a pre-determined threshold value. If so, in a fourth step 404 a signal and/or alert is generated and in a fifth step 405, the animal which has a water uptake value which is deviating from the mean value or the value deduced therefrom is identified. It is to be noted that the different method steps illustrated in FIG. 4 not necessarily all need to occur in the order illustrated. For instance, steps 404 and 405 may occur in the inverse order, or may occur simultaneously.

Figure 2:
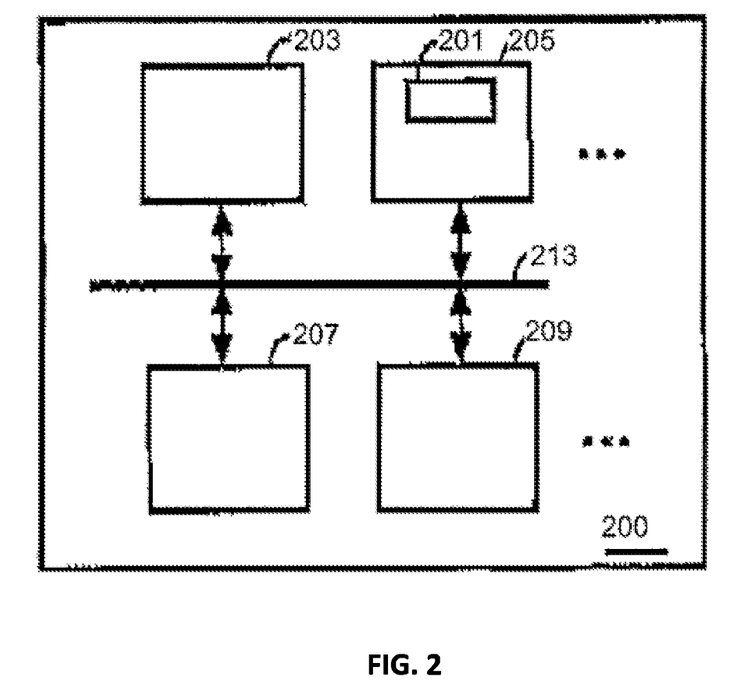
FIG. 2 schematically represents an electronic computing system (e.g. PDA, smartphone, laptop, PC, etc.) for use with the present invention.

The above-described method embodiments of the present invention may be implemented in a processing system (unit) 200 such as shown in FIG. 2. FIG. 2 shows one configuration of processing system 200 that can be implemented on an electronic processing system, for instance a mobile phone, a PDA, a laptop, a personal computer etc. It includes at least one programmable processor 203 coupled to a memory subsystem 205 that includes at least one form of memory, e.g., RAM, ROM, and so forth. It is to be noted that the processor 203 or processors may be a general purpose, or a special purpose processor, and may be for inclusion in a device, e.g., a chip that has other components that perform other functions. The processor may also be an FPGA or other programmable logic device. Thus, one or more aspects of the present invention can be implemented in digital electronic circuitry, or in computer hardware, firmware, software, or in combinations of them. The processing system may include a storage subsystem 207 that may have at least one disk drive and/or CD-ROM drive and/or DVD drive and/or USB port. In some implementations, a display system, a keyboard, and a pointing device or a touch screen may be included as part of a user interface subsystem 209 to provide for a user to manually input information. Ports for inputting and outputting data also may be included, for instance interfaces for one or more microphones for capturing sound signals, especially water or liquid uptake sounds from an animal or group of animals, particularly sheep or goats). Further interfaces may be provided for coupling image capturing devices to the computer system, e.g. for connection to a digital camera or cameras, e.g. a video camera. More elements such as network connections, interfaces to various devices, and so forth, may be included, either by wire line or wireless connections, but are not illustrated in FIG. 2. The various elements of the processing system 200 may be coupled in various ways, including via a bus subsystem 213 shown in FIG. 2 for simplicity as a single bus, but will be understood to those in the art to include a system of at least one bus. The memory of the memory subsystem 205 may at some time hold part or all (in either case shown as 201) of a set of instructions that when executed on the processing system 200 implement the steps of the method embodiments described herein.

The present invention also includes a computer program product, which provides the functionality of any of the methods according to the present invention when executed on a computing device. Such computer program product can be tangibly embodied in a carrier medium carrying machine-readable code for execution by a programmable processor. The present invention thus relates to a carrier medium carrying a computer program product that, when executed on computing means, provides instructions for executing any of the methods as described above. The term "carrier medium" refers to any medium that participates in providing instructions to a processor for execution. Such a medium may take many forms, including but not limited to, non-volatile media, and transmission media. Non-volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

The invention claimed is:

1. A pregnancy toxaemia determining system for automatically determining pregnancy toxaemia in at least one animal in a group of animals, the system comprising:
    a sensor for obtaining at least one value representative of a liquid or water uptake of the at least one animal, said sensor being adapted to be positioned in a vicinity of a liquid or water supply station or on the at least one animal; and
    a processing unit configured for
    comparing the obtained at least one value representative of a liquid or water uptake of the at least one animal to a mean value representative of an average of the at least one value for the group of animals or to a value deduced therefrom; and
    generating a signal and/or alert when the obtained at least one value representative of a liquid or water uptake exceeds the mean value or the value deduced therefrom by a pre-determined threshold value, wherein the pre-determined threshold value is selected such that the obtained at least one value representative of a liquid or water uptake must exceed the mean value by at least 20% before generating the signal and/or alert.

2. The pregnancy toxaemia determining system according to claim 1, further comprising an identification unit for identifying the at least one animal, the identification unit being adapted to be positioned in the vicinity of the liquid or water supply station or on the at least one animal, wherein the processing unit is configured for determining the at least one animal for which the signal and/or alert is generated.

3. The pregnancy toxaemia determining system according to claim 1, further comprising a breath analyzer for analyzing a breath of the at least one animal.

4. The pregnancy toxaemia determining system according to claim 1, wherein the sensor is provided in a compact cylindrical valve device that is adapted to be removably attached directly to a water supply line and is arranged to deliver water, on demand, into the at least one animal's mouth through a hollow control device and is adapted to obtain the at least one value representative of a liquid or water uptake.

5. A non-transitory data carrier storing a computer program product implemented on the sensor and processing unit of the system according to claim 1, wherein the computer program product enables performing a method for automatically
    monitoring pregnancy toxaemia in the at least one animal in the group of animals, the method comprising:
    obtaining from the sensor at least one value representative of a liquid or water uptake of the at least one animal;
    comparing in the processor the obtained at least one value representative of a liquid or water uptake to a mean value representative of an average of the at least one value for the group of animals or to a value deduced therefrom; and
    generating a signal and/or alert when the at least one value representative of a liquid or water uptake exceeds the mean value or the value deduced therefrom by a pre-determined threshold value, indicative of pregnancy toxaemia of the at least one animal;
    wherein the pre-determined threshold value is selected such that the obtained at least one value representative of a liquid or water uptake must exceed the mean value by at least 20% before generating the signal and/or alert.

6. A water supply station for at least one animal in a group of animals, said water supply station comprising:
    an identification unit for identifying the at least one animal approaching or standing at the water supply station;
    a sensor for obtaining at least one value representative of a liquid or water uptake of the at least one animal;
    a processing unit configured for comparing the obtained at least one value representative of a liquid or water uptake of the at least one animal to a mean value representative of an average of the at least one value for the group of animals or to a value deduced therefrom; and
    generating a signal and/or alert when the obtained at least one value representative of a liquid or water uptake exceeds the mean value or the value deduced therefrom by a predetermined threshold value;
    wherein the pre-determined threshold value is selected such that the obtained at least one value representative of a liquid or water uptake must exceed the mean value by at least 20% before generating the signal and/or alert.

7. The water supply station according to claim 6, further comprising a breath analyzer for analyzing a breath sample of the at least one animal.

8. The water supply station according to claim 6, wherein the sensor is provided in a compact cylindrical valve device that is adapted to be removably attached to a water supply line and is arranged to deliver water, on demand, into the at least one animal's mouth through a hollow control device and is adapted to obtain the at least one value representative of a liquid or water uptake.

9. A water dispenser comprising a sensor, wherein the water dispenser comprises a compact cylindrical valve device that is adapted to be removably attached to a water supply line and is arranged to deliver water, on demand, into at least one animal's mouth through a hollow control device and wherein the sensor is provided so as to obtain at least one value representative of a liquid or water uptake of the at least one animal;
  wherein said water dispenser is adapted to communicate with or comprises a processing unit configured for:
  comparing the obtained at least one value representative of a liquid or water uptake of the at least one animal to a mean value representative of an average of the at least one value for a group of animals comprising the at least one animal or to a value deduced therefrom; and
  generating a signal and/or alert when the obtained at least one value representative of a liquid or water uptake of the at least one animal exceeds the mean value or the value deduced therefrom by a pre-determined threshold value;
  wherein the pre-determined threshold value is selected such that the obtained at least one value representative of a liquid or water uptake must exceed the mean value by at least 20% before generating the signal and/or alert.

10. Use of a value representative for liquid or water uptake of an animal as an indication of a presence of pregnancy toxaemia of said animal, the use comprising the step of: comparing the value representative for liquid or water uptake of the animal to a mean value representative of an average of the value for a group of animals comprising the animal or to a value deduced therefrom.

11. Use according to claim 10, wherein said animal is a pregnant ewe or doe.

12. Use according to claim 10, wherein the value representative for liquid or water uptake is liquid or water uptake frequency.

13. A pregnancy toxaemia determining method for automatically monitoring pregnancy toxaemia in at least one animal in a group of animals, the method comprising:
  obtaining at least one value representative of a liquid or water uptake of the at least one animal;
  comparing the obtained at least one value representative of a liquid or water uptake to a mean value representative of an average of the at least one value for the group of animals or to a value deduced therefrom;
  generating a signal and/or alert when the at least one value representative of a liquid or water uptake exceeds the mean value or the value deduced therefrom by a pre-determined threshold value, indicative of pregnancy toxaemia of the at least one animal;
  wherein the pre-determined threshold value is selected such that the obtained at least one value representative of a liquid or water uptake must exceed the mean value by at least 20% before generating the signal and/or alert.

14. The pregnancy toxaemia determining method for automatically monitoring pregnancy toxaemia according to claim 13, wherein the at least one value representative of a liquid or water uptake is a drinking frequency, drinking time, drinking volume or a combination thereof.

* * * * *